(12) United States Patent
Boudreaux

(10) Patent No.: US 11,076,878 B2
(45) Date of Patent: *Aug. 3, 2021

(54) SURGICAL DEVICE WITH ANTI-BINDING FEATURES

(71) Applicant: Ethicon LLC, Guaynabo, PR (US)

(72) Inventor: Chad P. Boudreaux, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 205 days.

This patent is subject to a terminal disclaimer.

(21) Appl. No.: 16/197,941

(22) Filed: Nov. 21, 2018

(65) Prior Publication Data

US 2019/0090896 A1 Mar. 28, 2019

Related U.S. Application Data

(63) Continuation of application No. 14/950,969, filed on Nov. 24, 2015, now Pat. No. 10,136,910.

(51) Int. Cl.
*A61B 17/295* (2006.01)
*A61B 17/32* (2006.01)
(Continued)

(52) U.S. Cl.
CPC ............ *A61B 17/295* (2013.01); *A61B 17/29* (2013.01); *A61B 17/320016* (2013.01);
(Continued)

(58) Field of Classification Search
CPC ... A61B 17/29; A61B 17/2909; A61B 17/295; A61B 17/320016; A61B 17/32002; A61B 2017/07285; A61B 2017/2901; A61B 2017/2902; A61B 2017/2912; A61B 2017/2919; A61B 2017/292;
(Continued)

(56) References Cited

U.S. PATENT DOCUMENTS 5,254,129 A 10/1993 Alexander
5,445,638 A 8/1995 Ryden et al.
(Continued)

FOREIGN PATENT DOCUMENTS

CN 102647949 A 8/2012
CN 103717147 A 4/2014
(Continued)

OTHER PUBLICATIONS

International Search Report and Written Opinion for PCT/US2016/060909 dated May 29, 2018 (12 pages).
(Continued)

*Primary Examiner* — Ryan J. Severson
(74) *Attorney, Agent, or Firm* — Mintz Levin Cohn Ferris Glovsky and Popeo, P.C.

(57) ABSTRACT

Methods and devices are provided for preventing binding between components of a drive assembly of a surgical device. In an exemplary embodiment, a surgical device is provided having a ball-and-socket joint that allows bending of various drive shafts relative to the handle without causing movement of a drive rack disposed within the handle. Since the drive rack does not move in response to bending of the shaft, the drive gear and rack will remain aligned thus preventing jamming of the device.

20 Claims, 5 Drawing Sheets

(51) Int. Cl.
*A61B 17/29* (2006.01)
*A61B 17/00* (2006.01)

(52) U.S. Cl.
CPC .............. *A61B 2017/00473* (2013.01); *A61B 2017/2902* (2013.01); *A61B 2017/2923* (2013.01); *A61B 2017/320028* (2013.01)

(58) Field of Classification Search
CPC .... A61B 2017/2923; A61B 2017/2926; A61B 2017/2932; A61B 2017/2939; A61B 2017/2943; A61B 2017/320028; A61B 2017/320032; A61B 2018/00607; A61B 2018/1452; A61B 2018/1455; A61B 2018/1457
See application file for complete search history.

(56) References Cited

U.S. PATENT DOCUMENTS

| | | | |
|---|---|---|---|
| 5,458,598 | A | 10/1995 | Feinberg et al. |
| 5,599,350 | A | 2/1997 | Schulze et al. |
| 5,665,100 | A | 9/1997 | Yoon |
| 5,797,938 | A | 8/1998 | Paraschac et al. |
| 5,797,941 | A | 8/1998 | Schulze et al. |
| 5,800,449 | A | 9/1998 | Wales |
| 5,913,874 | A | 6/1999 | Berns et al. |
| 5,919,202 | A | 7/1999 | Yoon |
| 5,964,758 | A | 10/1999 | Dresden |
| 5,984,938 | A | 11/1999 | Yoon |
| 6,004,335 | A | 12/1999 | Vaitekunas et al. |
| 6,358,268 | B1 | 3/2002 | Hunt et al. |
| 6,558,385 | B1 | 5/2003 | McClurken et al. |
| 6,679,882 | B1 | 1/2004 | Kornerup |
| 7,364,061 | B2* | 4/2008 | Swayze ............ A61B 17/07207 227/176.1 |
| 7,455,208 | B2* | 11/2008 | Wales ............... A61B 17/07207 227/178.1 |
| 7,784,662 | B2 | 8/2010 | Wales et al. |
| 8,133,224 | B2 | 3/2012 | Geiselhart |
| 8,142,474 | B2 | 3/2012 | Hafner |
| 8,287,536 | B2 | 10/2012 | Mueller et al. |
| 8,439,911 | B2 | 5/2013 | Mueller |
| 8,523,898 | B2 | 9/2013 | Bucciaglia et al. |
| 8,613,752 | B2 | 12/2013 | Kamel |
| 8,795,275 | B2 | 8/2014 | Hafner |
| 8,864,795 | B2 | 10/2014 | Kerr et al. |
| 8,906,018 | B2 | 12/2014 | Rooks et al. |
| 8,939,974 | B2 | 1/2015 | Boudreaux et al. |
| 8,968,359 | B2 | 3/2015 | Kerr et al. |
| 8,992,526 | B2 | 3/2015 | Brodbeck et al. |
| 9,504,519 | B2 | 11/2016 | Kerr et al. |
| 9,585,714 | B2 | 3/2017 | Livneh |
| 9,788,848 | B2 | 10/2017 | Ward et al. |
| 10,136,910 | B2* | 11/2018 | Boudreaux ........... A61B 17/295 |
| 2006/0190031 | A1 | 8/2006 | Wales et al. |
| 2006/0229665 | A1 | 10/2006 | Wales et al. |
| 2008/0015566 | A1 | 1/2008 | Livneh |
| 2009/0043305 | A1 | 2/2009 | Brodbeck et al. |
| 2009/0202387 | A1 | 8/2009 | Dlugos, Jr. et al. |
| 2009/0299353 | A1 | 12/2009 | Lewinsky et al. |
| 2009/0326531 | A1 | 12/2009 | Geiselhart |
| 2010/0016879 | A1 | 1/2010 | Hafner |
| 2010/0030213 | A1 | 2/2010 | Hafner |
| 2011/0006101 | A1 | 1/2011 | Hall et al. |
| 2011/0054467 | A1 | 3/2011 | Mueller et al. |
| 2011/0060333 | A1 | 3/2011 | Mueller |
| 2011/0087208 | A1 | 4/2011 | Boudreaux et al. |
| 2011/0087218 | A1 | 4/2011 | Boudreaux et al. |
| 2012/0095460 | A1 | 4/2012 | Rooks et al. |
| 2012/0271332 | A1 | 10/2012 | Kamel |
| 2013/0085516 | A1 | 4/2013 | Kerr et al. |
| 2013/0304041 | A1 | 11/2013 | Merz et al. |
| 2015/0066076 | A1 | 3/2015 | Kerr et al. |
| 2015/0094720 | A1 | 4/2015 | Rooks et al. |
| 2015/0148804 | A1 | 5/2015 | Rooks et al. |
| 2015/0272660 | A1 | 10/2015 | Boudreaux et al. |
| 2016/0000496 | A1 | 1/2016 | Kerr et al. |
| 2017/0071657 | A1 | 3/2017 | Kerr et al. |
| 2017/0143361 | A1* | 5/2017 | Boudreaux ........... A61B 17/295 |
| 2019/0090896 | A1* | 3/2019 | Boudreaux ........... A61B 17/295 |

FOREIGN PATENT DOCUMENTS

| | | |
|---|---|---|
| CN | 104768481 A1 | 7/2015 |
| JP | 2013070861 A | 4/2013 |
| WO | 2015069719 A1 | 5/2015 |
| WO | 2017091346 A1 | 6/2017 |

OTHER PUBLICATIONS

International Preliminary Report for PCT/US2016/060909 dated May 29, 2018, (9 pages).

* cited by examiner

SURGICAL DEVICE WITH ANTI-BINDING FEATURES

CROSS-REFERENCE TO RELATED APPLICATIONS

This application is a continuation of U.S. patent application Ser. No. 14/950,969, filed Nov. 24, 2015, entitled "SURGICAL DEVICE WITH ANTI-BINDING FEATURES," which is herein incorporated by reference in its entirety.

FIELD

Surgical devices and methods having anti-binding features are provided.

BACKGROUND

Endoscopic surgical instruments are often preferred over traditional open surgical devices since a smaller incision, or incisions, associated with endoscopic surgical techniques tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Endoscopic devices are passed through an access port, such as a trocar, to allow the distal end effector to engage tissue within a body cavity of a patient. The tissue can also be cut using a cutting element, such as a knife. Loading forces experienced by a shaft of the device as the end effector engages the tissue may cause the shaft to bend relative to the handle and to thus result in jamming or binding between components participating in distal advancement and proximal return of the cutting element. As a result, the cutting element can be prevented from being properly used to cut tissue. As another undesirable consequence, if the binding occurs during advancement or retraction of the cutting instrument, the device cannot be removed because the cutting element cannot be properly returned to its default position. The surgeon may be forced to open up the patient and manipulate the instrument, potentially causing serious harm to the patient.

Accordingly, there remains a need for methods and devices for preventing binding of components of a cutting assembly of a surgical device.

SUMMARY

Various methods and devices are provided for preventing binding or jamming of components of a cutting assembly of a surgical device.

In one aspect, a surgical device is provided that includes a handle, an end effector, a closure tube, a knife pusher shaft, and a rack. The handle has an elongate shaft extending distally therefrom. The end effector is disposed at a distal end of the elongate shaft and has first and second jaws that are movable between an open configuration and a closed configuration in which the first and second jaws are configured to engage tissue therebetween. The closure tube extends through the handle and the elongate shaft and is configured to move the first and second jaws between the open configuration and the closed configuration. The knife pusher shaft is disposed at least partially around the closure tube and is configured to move a cutting element through the first and second jaws for cutting tissue engaged therebetween. The rack is coupled to the knife pusher shaft by a ball-and-socket joint such that the knife pusher shaft can pivot relative to the rack. Movement of the rack is effective to drive the knife pusher shaft and thereby move the cutting element through the first and second jaws.

The surgical device can vary in any number of ways. For example, the surgical device can include a gear disposed within the handle and engaged with the rack for driving the rack. In one embodiment, the handle can include a motorized drive assembly that is effective to rotate the gear. The rack can have various configurations, for example, it be formed along an external surface of an elongate housing having a cylindrical cavity formed therethrough that receives the closure tube. In such an example, the ball-and-socket joint can include a spherical cavity formed in a distal end of the elongate housing, and a spherical ball formed on a proximal end of the knife pusher shaft and pivotally seated within the spherical cavity.

The housing can also have various configurations, and in one embodiment it includes a stationary handle and a movable handle that is configured to pivot toward the stationary handle to move the closure tube proximally and thereby move the first and second jaws to the closed configuration.

In another aspect, a surgical device is provided that includes a handle, a jaw closure assembly, and a cutting assembly. The handle can have an elongate shaft extending distally therefrom and an end effector located on a distal end of the elongate shaft. The end effector can include first and second jaws that are movable between an open configuration and a closed configuration in which the first and second jaws are configured to engage tissue therebetween. The jaw closure assembly can extend through the handle and the elongate shaft and it can be configured to move the first and second jaws between the open and closed positions. The cutting assembly can extend through the handle and the elongate shaft and it can have a gear and a rack configured to drive a cutting element through the first and second jaws to cut tissue engaged between the jaws. The cutting assembly can also include a ball-and-socket joint located within the handle that prevents binding between the gear and rack.

The surgical device can vary in any number of ways. For example, the cutting assembly can include a knife pusher tube having a ball formed on a proximal end thereof, and the rack can be formed on a housing having a socket formed therein that seats the ball. In another example, the jaw closure assembly can include a closure tube extending through the handle and the elongate shaft and it can be configured to move the first and second jaws between the open configuration and the closed configuration. The closure tube can extend through the knife pusher tube and the housing. In one embodiment, the surgical device can include a motorized drive assembly disposed within the handle and effective to rotate the gear.

Methods for treating tissue are also provided. In one embodiment, the method includes engaging tissue between first and second jaws of an end effector on a distal end of an elongate shaft of a surgical device, and manipulating the surgical device to move the tissue. A force applied to the elongate shaft causes a knife pusher shaft extending therethrough to pivot about a pivot joint relative to a rack housing disposed within the handle. In one embodiment, the pivot joint is a ball-and-socket joint formed between the knife pusher shaft and the rack housing.

The method can vary in any number of ways. For example, the method can further include activating the surgical device to rotate a gear within the device such that the gear drives the rack housing and the knife pusher coupled thereto to move a cutting element through the first and second jaws and thereby cut the tissue engaged therebetween. In one embodiment, the surgical device can include a motor, and activating the device can cause a power source to deliver energy to the motor such that the motor drives the gear.

In other aspects, engaging tissue between the first and second jaws can include moving a movable handle toward a stationary handle to move a jaw closure shaft proximally. Proximal movement of the jaw closure shaft can cause the first and second jaws to approximate to engage the tissue. The jaw closure shaft can move proximally through the knife pusher shaft and the rack housing when the movable handle is moved toward the stationary handle.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Figure 1:
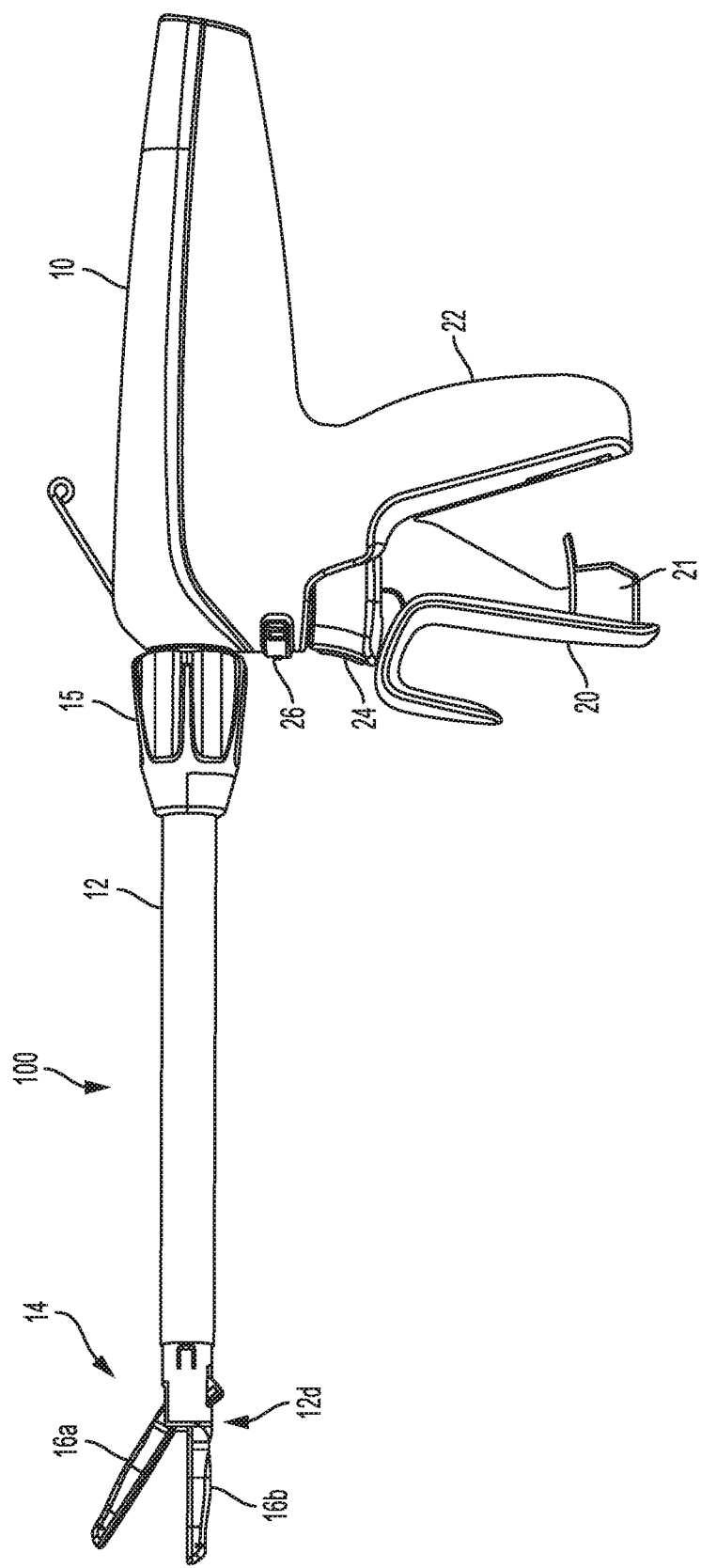
FIG. 1 is a side view of one embodiment of a surgical device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon.

Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices are provided for preventing binding or jamming of components of a drive assembly of a surgical device due to load on a shaft of the device. In an exemplary embodiment, the surgical has a handle with an elongate shaft extending distally therefrom and an end effector located on a distal end of the elongate shaft. The end effector includes first and second jaws that are movable between an open configuration and a closed configuration in which the first and second jaws are configured to engage tissue therebetween. The surgical device also includes, among other components, a cutting assembly extending through the handle and the elongate shaft and having a gear and a rack housing configured to drive a cutting element through the jaws to cut tissue engaged between the jaws. In an exemplary embodiment, the cutting assembly includes a ball-and-socket joint located within the handle that prevents binding between the gear and the rack. Thus, components of the cutting assembly are not affected by possible bending of the elongate shaft of the surgical instrument due to load applied thereto in various surgical environments. This allows for proper advancement of the cutting element to cut tissue engaged between the jaws. Furthermore, the ball-and-socket joint configuration allows the cutting element to be properly retracted after it is used to cut the tissue.

Figure 2:
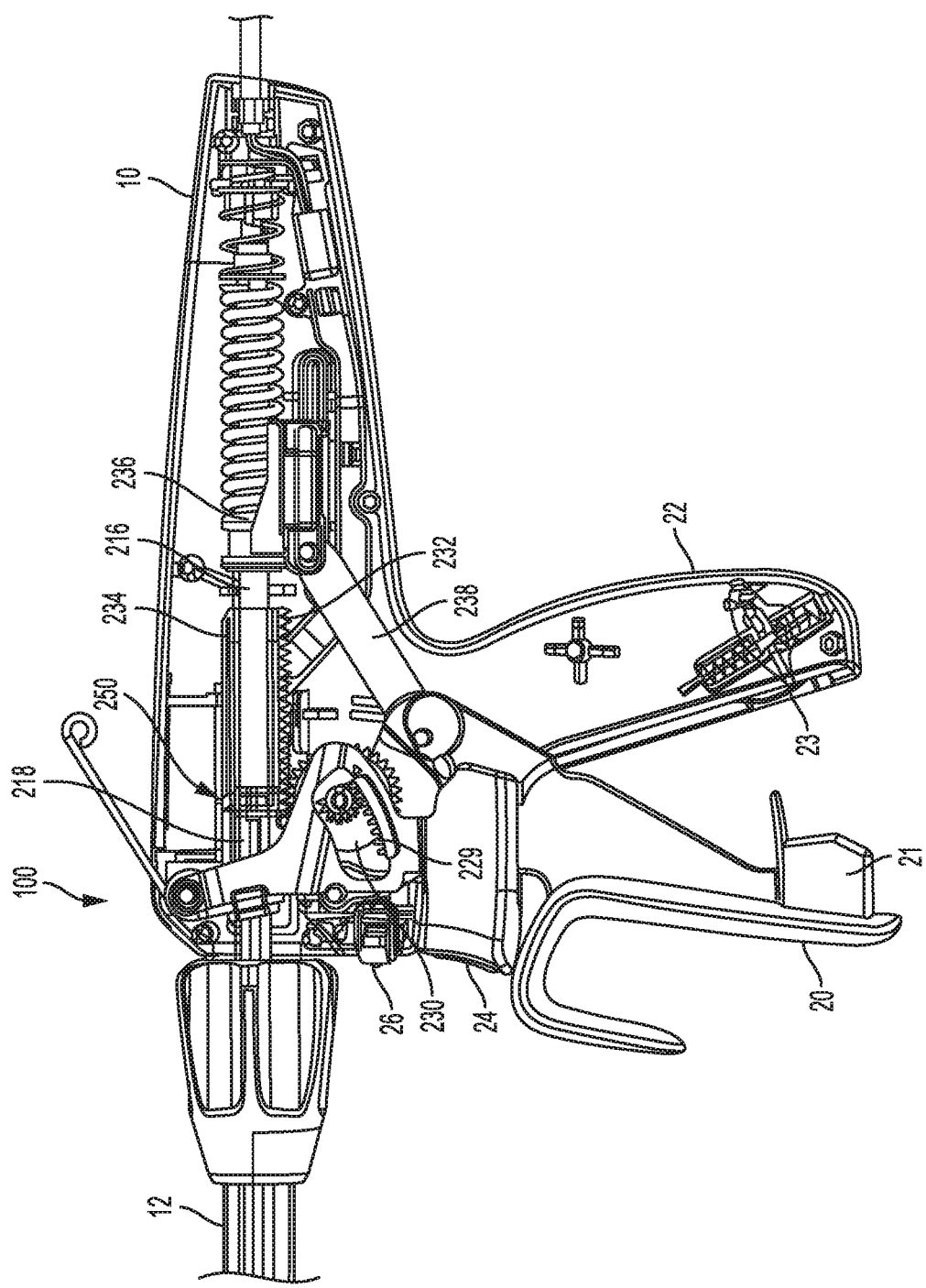
FIG. 2 is a side view of a handle portion of the surgical device of FIG. 1, with various components removed for clarity.

FIGS. 1 and 2 illustrate one embodiment of a surgical device configured to grasp and cut tissue. As shown, the illustrated surgical device 100 generally includes a proximal handle 10, a shaft 12 extending distally from the proximal handle 10, and an end effector 14 for grasping tissue. The proximal handle 10 can be any type of pistol-grip, scissor grip, pencil-grip, or other type of handle known in the art that is configured to carry various actuators, such as actuator levers, knobs, triggers, or sliders, for actuating various functions such as rotating, articulating, approximating, and/or firing the end effector 14. In the illustrated embodiment, the proximal handle 10 includes a stationary handle 22 and a closure actuator 20 in the form of a handle that is movable toward and away from the stationary handle 22 to open and close the jaws of the end effector 14. The illustrated proximal handle 10 also includes a rotation knob 15 that is configured to rotate the shaft 12, a firing actuator 24 that is configured to drive a cutting element through the end effector, and an energy actuator 26 that is configured to cause energy to be delivered to tissue engaged between the jaws of the end effector 14. The various actuators can be coupled to the end effector by one or more drive assembly extending through the handle and through the elongate shaft 12.

The end effector can have a variety of sizes, shapes, and configurations. As shown in FIG. 1, the end effector 14 includes a first, upper jaw 16a in the form of an anvil and a second, lower jaw 16b that houses a staple cartridge with staples. The jaws are disposed at a distal end 12d of the shaft 12. The jaws 16a, 16b are movable between an open position in which the jaws 16*a*, 16*b* are spaced a distance apart, and a closed position in which the jaws 16*a*, 16*b* are moved toward one another and are substantially opposed. When the jaws 16*a*, 16*b* are in the closed position, a longitudinal axis of the upper jaw 16*a* can be substantially parallel to a longitudinal axis of the lower jaw 16*b* and the jaws 16*a*, 16*b* can be in direct contact for engaging tissue therebetween. In the illustrated embodiment, the upper jaw 16*a* pivots relative to the shaft 12 and relative to the lower jaw 16*b* while the lower jaw 16*b* remains stationary, however in other embodiments the lower jaw can pivot relative to the upper stationary jaw, or both jaws can pivot. While the illustrated jaws 16*a*, 16*b* have a substantially elongate and straight shape, a person skilled in the art will appreciate that one or both of the jaws 16*a*, 16*b* can be curved and/or can extend in various directions. The jaws 16*a*, 16*b* can have any suitable axial length for engaging tissue, and the length can be selected based on the targeted anatomical structure for transection and/or sealing.

As indicated above, the surgical device 100 has a stationary handle 22 that is configured to open and close the jaws 16*a*, 16*b* of the end effector 14. Manipulation of the closure actuator 20 can pivot or otherwise move the jaws relative to one another such that the jaws can engage tissue, move anatomical structures, or perform other surgical functions. The closure actuator 20 can have various sizes, shapes, and configurations, but in the illustrated embodiment the closure actuator 20 pivots about a pivot point to move toward and away from stationary handle 22. In particular, the closure actuator 20 can have a first position in which it is angularly offset and spaced apart from the stationary handle 22. In this position, as shown in FIG. 1, the jaws 16*a*, 16*b* of the end effector 14 are open. The closure actuator 20 can have a second position where it is positioned adjacent to, or substantially in contact with, the stationary handle 22. In this position, the jaws 16*a*, 16*b* of the end effector 14 are approximated to the closed position to engage tissue and apply a force to tissue disposed therebetween. The closure actuator 20 can be biased to the first open position with the jaws 16*a*, 16*b* of the end effector 14 being open, as shown in FIG. 1. The closure actuator 20 can also include a locking mechanism for maintaining the closure actuator 20 in the second position. As shown in FIG. 2, the stationary handle includes a locking element 23 that is configured to engage a locking feature 21 on the closure actuator 20 to lock the closure actuator 20 relative to the stationary handle 22. The illustrated locking mechanism is configured to automatically engage when the closure actuator 20 substantially contacts the stationary handle 22, however, in other embodiments, the locking mechanism can automatically engage at each position the closure actuator 20 is pivoted through, such as via ratcheting.

In order to effect closing of the jaws, the closure actuator 20 can be coupled to a drive assembly that is operatively associated with the jaws to move the jaws between the open and closed positions. In the embodiment shown in FIG. 2, the closure actuator 20 is coupled to a yoke 236 via a linkage 238. The yoke 236 in turn is coupled to a jaw closure tube 216, that extends through the handle 10 and the elongate shaft 12 and that is coupled to the first jaw 16*a*. Movement of the closure actuator 20 toward the stationary handle 22 will move the linkage 238 and thus the yoke 236 proximally, thereby moving the closure tube 216 proximally. The closure tube 216 will in turn pull the proximal end of the first jaw 16*a* to cause the jaw to move to the closed position. The locking mechanism will maintain the closure actuator 20 in the second configuration adjacent to the stationary handle 22. A person skilled in the art will appreciate that the drive assembly can have a variety of other configurations and various drive mechanisms, including a drive screw, motorized drive assemblies, other gears configurations, etc., can be used.

As also indicated above, the surgical device 100 has a cutting assembly that includes a firing actuator 24 that is configured to advance a cutting element through the jaws 16*a*, 16*b* to cut tissue engaged therebetween. The firing actuator 24 can have various sizes, shapes, and configurations, but in the illustrated embodiment it is in the form of a button or trigger that can be depressed and move proximally into the housing. In another embodiment, the firing actuator 24 can be in the form of a switch, lever, etc., that can be slid, pivoted, or otherwise moved by a user. Depressing or pivoting the firing actuator 24 can cause a cutting assembly to advance through the end effector. As shown in FIG. 2, the firing actuator 24 has a cut-out formed therein and defining a firing rack 229. The firing rack 229 is coupled to a gear 230 via one or more additional gears. Gear 230 has teeth formed thereon that threadably engage a toothed drive rack 232 that is formed on an elongate rack housing 234. When the firing actuator 24 is pivoted proximally, the firing rack 229 drives the gear 230 (via one or more additional gears), and rotation of the gear 230 drives the rack housing 234 distally.

Figure 3:
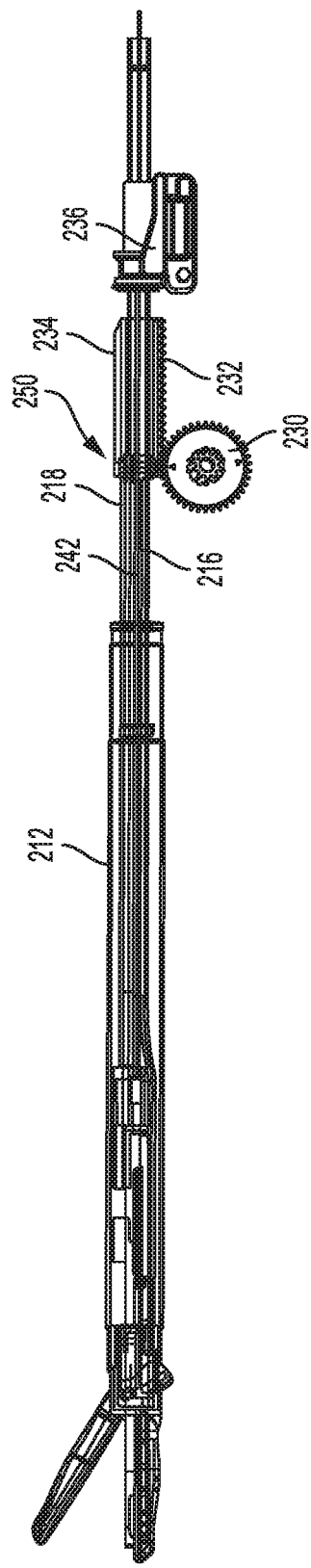
FIG. 3 is a side, partially transparent view of various components of the surgical device of FIGS. 1 and 2.
Figure 4:
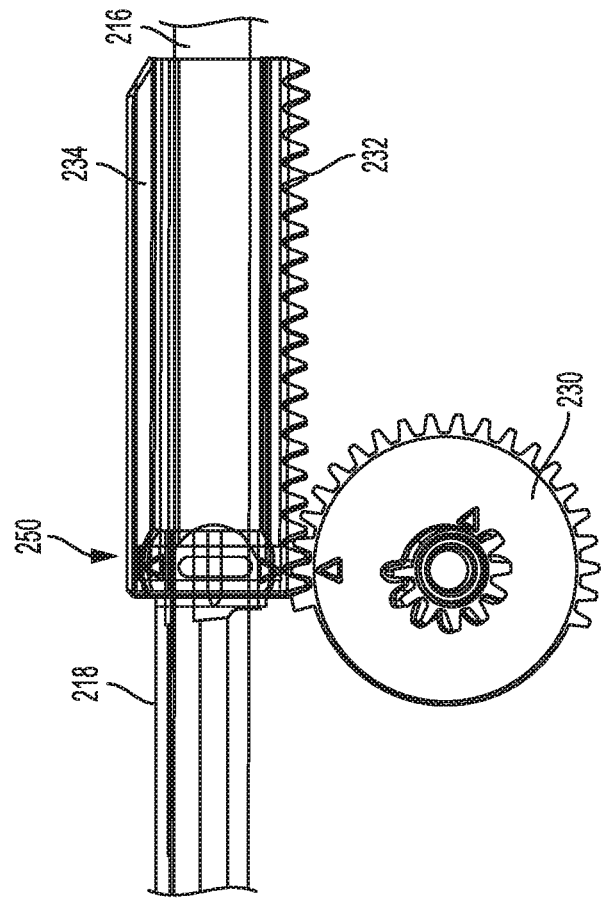
FIG. 4 is a side view of a ball-and-socket joint and a gear of the surgical device of FIGS. 1 and 2.

Advancement of the rack housing 234 drives a cutting assembly through the first and second jaws to cut tissue engaged between the jaws. While the cutting assembly can have various configurations, as shown in more detail in FIG. 3, the cutting assembly generally includes a knife pusher shaft 218 that is coupled at its proximal end to the rack housing 234 and at its distal end to a cutting element. The knife pusher shaft 218 is generally in the form of an elongate hollow shaft having the jaw closure tube 216 extending therethrough. As shown in FIG. 3, the jaw closure tube 216 extends proximally beyond the knife pusher shaft 218, through the rack housing 234, and proximally beyond the rack housing 234 to couple to the yoke 236 that is driven by the closure actuator 20 via the linkage 238.

The cutting element or knife 242 can have any suitable configuration for transecting tissue captured between the jaws, and it can be sized and shaped to transect or cut various thicknesses and types of tissue. In an exemplary embodiment, the cutting assembly includes a cutting element having a sharp or serrated edge configured to transect the tissue. In some embodiments, the cutting assembly can include, for example, an E-beam compression member that travels through slots formed in each jaw to pull the jaws into a parallel orientation and to compress tissue therebetween. The cutting element can be coupled to or integrally formed on the compression member. In other embodiments, the cutting assembly can include a shaft having a knife blade that is not attached to a compression member such that the cutting assembly can advance and retract relative to the jaws without applying compression to the tissue.

As further noted above, the device 100 can also include a third actuator in the form of an energy actuator 26 that is effective to cause energy to be delivered to tissue engaged between the jaws. The energy actuator 26 can be configured to operatively couple to a generator, which can be a separate unit that is electrically connected to the surgical device 100. The energy actuator 26 and the generator can be operatively coupled so that the device is configured to apply energy to tissue engaged by the end effector when the energy actuator 26 is activated. The generator can be any suitable generator known in the art, such as an RF generator, an ultrasound generator, or other type of a generator. A lumen (not shown) of the shaft 12 can carry electrical leads or wires that can deliver electrical energy to components of the end effector 14.

While not shown, a person skilled in the art will appreciate that the jaw closing assembly and/or the cutting assembly can be powered rather than being manually driven. For example, the closure actuator can be coupled to a motor disposed in the proximal handle 10 and manual movement of the closure actuator 20 can cause a processor to send a control signal to the motor, which can interact with various gears or other components to cause the jaws 16a, 16b to open and close. By way of further example, the firing actuator 24 can be in electrical communication with a motor disposed in the proximal handle 10 and activation of the firing actuator 24 can similarly activate the motor which can be operatively coupled to one or more gears and a rack for driving a cutting element through the jaws. Energy delivery can likewise be controlled by a processor that controls the closure and/or firing systems. The device can also include other power-driven features, such as powered articulation and/or powered rotation of the end effector and/or shaft.

In an exemplary embodiment, the device 100 includes features that prevent binding of components of the cutting assembly. In particular, during use of the end effector to engage and manipulate tissue, a load is often applied to the elongate shaft 12 that can cause the elongate shaft 12 to bend or pivot relative to the handle 10. A person skilled in the art will appreciate that the term "bend" is used herein to refer to movement out of the longitudinal axis, including pivotal movement or flexion that causes various portions of the component to be misaligned with respect to its longitudinal axis. Since the jaw closure tube 216 extends through the rack housing 234 and through at least a portion of the knife pusher shaft 218, any bending of the elongate shaft 12, and thus the jaw closure tube 216 and knife pusher shaft 218 extending therethrough, will cause the rack housing 234 to bend or pivot out of axis. As a result, the drive rack 232 on the rack housing 234 will become misaligned with respect to the gear 230, thereby potentially resulting in jamming or binding of the gears. When the gear 230 is jammed or misaligned with the drive rack 232 on the rack housing 234, the firing actuator 24 will be prevented from driving the cutting element.

Accordingly, in an exemplary embodiment, the device 100 includes features to prevent such binding or jamming from occurring. Specifically, the knife pusher shaft 218 can be configured such that the bending of the knife pusher shaft 218 and the closure tube 216 disposed therein does not cause the rack housing 234 to bend or otherwise move out of axis. As shown in FIGS. 2-6, the knife pusher shaft 218 is coupled to the rack housing 234 by a ball-and-socket joint 250 such that the knife pusher shaft 218 can pivot or angulate relative to the rack housing 234. In this way, in the event the elongate shaft 12 of the surgical device 100 bends or otherwise moves, the rack housing 234 does not bend or move with it. The drive rack 232 and the gear 230 therefore remain in alignment.

Figure 5:
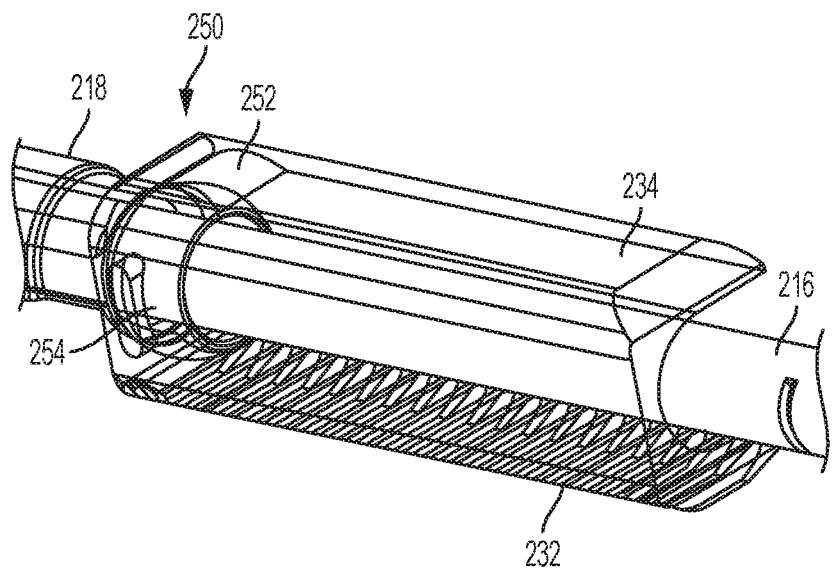
FIG. 5 is a perspective, transparent view of the ball-and-socket joint of FIG. 4.
Figure 6:
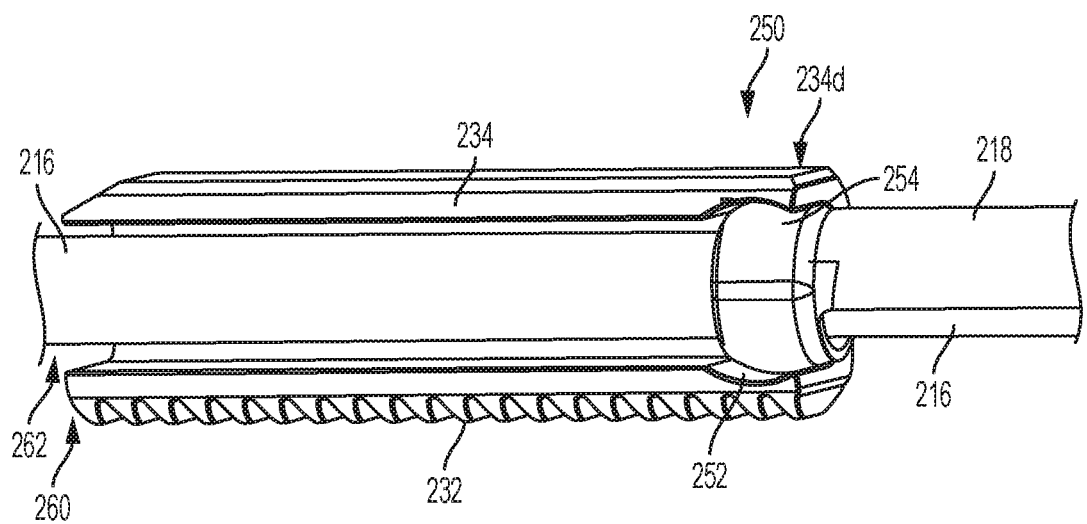
FIG. 6 is a side view of the ball-and-socket joint of FIG. 5.

FIGS. 4-8 illustrate the components of the ball-and-socket joint 250 in more detail. As shown, the ball-and-socket joint 250 includes a spherical socket or spherical cavity 252 formed in a distal end 234d of the elongate rack housing 234 having the drive rack 232 formed on an external surface thereof, and a spherical ball 254 formed on a proximal end 218p of the knife pusher shaft 218. As shown in FIGS. 5 and 6, the spherical ball 254 is pivotally seated within the spherical cavity 252 such that the knife pusher shaft 218 can pivot or angulate relative to the rack housing 234.

Figure 7:
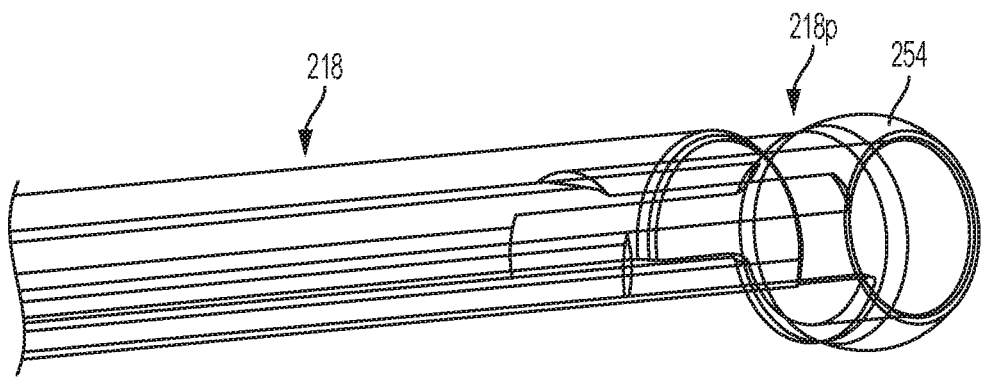
FIG. 7 is a perspective view of a knife pusher tube of the surgical device of FIGS. 1 and 2.

FIG. 7 illustrates the spherical ball 254 on the knife pusher shaft 218 in more detail. As shown, the knife pusher shaft 218 has a generally elongate cylindrical or semi-cylindrical configuration such that the knife pusher shaft 218 is disposed at least partially around the closure tube 216. While not shown, the distal portion of the knife pusher shaft can be in the form of a fully enclosed cylindrical tube. The spherical ball 254 is formed on the proximal end 218p of the knife pusher shaft 218 and is fully cannulated to receive the closure tube 216 therethrough. In the illustrated embodiment, the spherical ball 254 is integrally formed with the knife pusher shaft 218. However, it will be appreciated that the spherical ball 254 can be formed on the knife pusher shaft 218 in any suitable manner, for example, it can be coupled to the knife pusher shaft 218.

Figure 8:
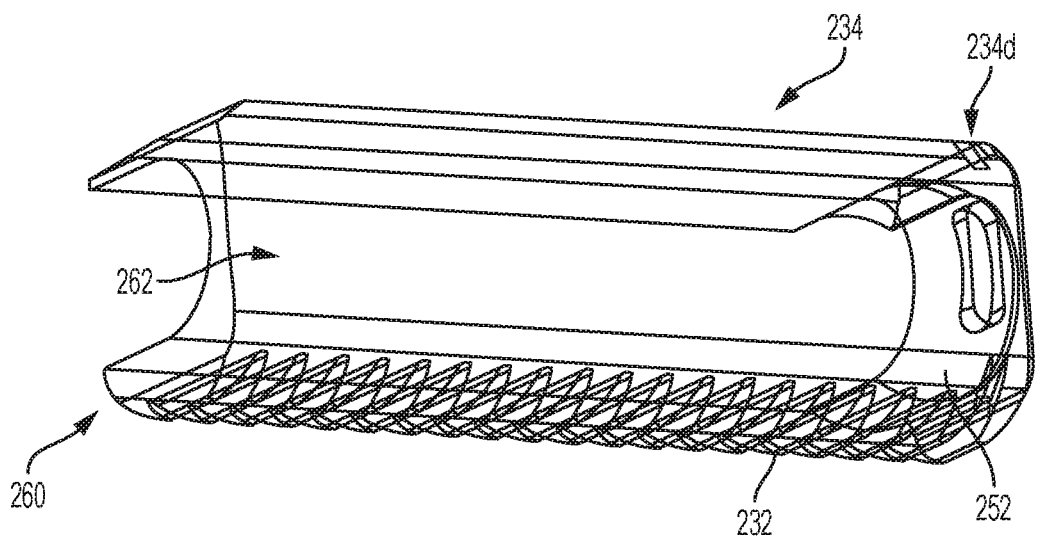
FIG. 8 is a perspective view of a rack housing of the surgical device of FIGS. 1 and 2.

The rack housing 234 is shown in more detail in FIG. 8. The drive rack 232 is formed along an external bottom surface 260 of the rack housing 234 such that the drive rack 232 faces and engages with the gear (e.g., gear 230 in FIGS. 2-4). The rack housing 234 has a generally elongate rectangular configuration with an elongate cavity 262 formed therethrough that receives the closure tube 216. The closure tube 216 thus extends through the knife pusher shaft 218 and the rack housing 234, as shown in FIGS. 5 and 6.

The spherical ball 254 formed on the proximal end 218p of the knife pusher shaft 218 and the spherical cavity 252 formed in the distal end 234d of the rack housing 234 can have any suitable size, but preferably the size is configured to allow free rotation of the knife pusher shaft 218 relative to the rack housing 234. The spherical cavity 252 can be formed on an inner wall of the cavity 262 in the rack housing 234 by forming concave seating surfaces within the inner wall, as shown in FIGS. 6 and 8. The spherical cavity 252 is sized and shaped to pivotally receive therein the spherical ball 254.

The spherical cavity 252 and the spherical ball 254 of the ball-and-socket joint 250 are configured such that the knife pusher shaft 218 can be disposed at various angles with respect to the rack housing. At the same time, the fit between the knife pusher shaft 218 and the drive rack 232 can be sufficiently tight, without a slack. The configuration of the ball-and-socket joint 250 allows the knife pusher shaft 218 and the closure tube 216 to bend without affecting a position of the rack housing 234. In this way, because the drive rack 232 and the gear 230 remain aligned, the gear 230 can drive the drive rack 232 to push the knife pusher shaft 218 as intended. Bending of the knife pusher shaft 218 and the closure tube 216 does not affect the movement of the rack housing 234.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices and components described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the described devices and methods based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A surgical device, comprising:
    a handle having an elongate shaft extending distally therefrom;
    an end effector at a distal end of the elongate shaft having first and second jaws that are movable between an open configuration for receiving tissue therebetween, and a closed configuration in which the first and second jaws are configured to engage tissue therebetween;
    a closure shaft extending through the elongate shaft and configured to translate proximally to move the first and second jaws form the open configuration to the closed configuration;
    a cutting shaft extending through the elongate shaft and a cutting element disposed in the end effector, the cutting shaft being distally movable to drive the cutting element distally through the end effector; and
    a cutting actuation assembly disposed in the handle and configured to distally advance the cutting shaft through the elongate shaft, the cutting actuation assembly and the cutting shaft being configured to remain in operable engagement when a load is applied to the cutting shaft that causes the cutting shaft to bend relative to a longitudinal axis thereof.

2. The device of claim 1, further comprising a gear and rack disposed within the handle and engaged with the cutting actuation assembly for distally advancing the cutting shaft.

3. The device of claim 1, wherein the cutting actuation assembly includes an elongate housing that operably engages the cutting shaft and has teeth formed therealong.

4. The device of claim 1, further comprising a joint disposed between the cutting actuation assembly and the cutting shaft.

5. The device of claim 4, wherein the joint is a ball-and-socket joint having a spherical cavity formed in a distal end of the cutting actuation assembly and a spherical ball formed on a proximal end of the cutting shaft, the spherical ball seated in and being configured to pivot relative to the spherical cavity.

6. The device of claim 1, wherein the handle comprises a stationary handle and a movable handle that is configured to pivot toward the stationary handle to move the first and second jaws from the open configuration to the closed configuration.

7. The device of claim 1, wherein the cutting actuation assembly includes a firing trigger configured to cause distal advancement of the cutting shaft through the elongate shaft upon actuation thereof.

8. A surgical device, comprising:
    a handle having an elongate shaft extending distally therefrom and an end effector located on a distal end of the elongate shaft, the end effector having first and second jaws that are movable between an open configuration for receiving tissue therebetween, and a closed configuration for engaging tissue therebetween,
    a closure tube extending between the handle and the end effector, the closure tube being configured to move proximally toward the hand to move the first and second jaws form the open configuration to the close configuration; and
    a cutting assembly having an actuation mechanism in the handle and a cutting shaft extending through the handle and the elongate shaft and configured to distally drive a cutting element through the first and second jaws to cut tissue engaged therebetween upon actuation of the actuation mechanism, the cutting assembly include a joint that allows the cutting shaft to bend relative to a longitudinal axis thereof while remaining in operable engagement with the actuation mechanism.

9. The device of claim 8, further comprising a gear and rack disposed within the handle and engaged with the actuation mechanism for distally advancing the cutting shaft.

10. The device of claim 8, wherein the actuation mechanism includes an elongate housing that operably engages the cutting shaft and has teeth formed therealong.

11. The device of claim 8, wherein the actuation mechanism includes a firing trigger configured to cause distal advancement of the cutting shaft through the elongate shaft upon actuation thereof.

12. The device of claim 8, wherein the joint is disposed between the cutting shaft and the actuation mechanism.

13. The device of claim 8, wherein the joint is a ball-and-socket joint having a spherical cavity formed in a distal end of the actuation mechanism and a spherical ball formed on a proximal end of the cutting shaft, the spherical ball seated in and being configured to pivot relative to the spherical cavity.

14. The device of claim 8, wherein the handle comprises a stationary handle and a movable handle that is configured to pivot toward the stationary handle to move the first and second jaws from the open configuration to the closed configuration.

15. A method for treating tissue, comprising:
    grasping tissue between first and second jaws of an end effector on a distal end of an elongate shaft of a surgical device by actuating a closure mechanism on the surgical device to move a jaw closure shaft proximally, the proximal movement of the jaw closure shaft causing the first and second jaws to approximate to engage the tissue; and manipulating the surgical device to move the tissue, wherein a force applied to the elongate shaft causes a knife pusher shaft extending therethrough to bend relative to a longitudinal axis thereof while remaining in operable engagement with an actuation mechanism in a handle of the surgical device.

16. The method of claim 15, wherein a joint is disposed between the knife pusher shaft and the actuation mechanism.

17. The method of claim 15, further comprising activating the surgical device to drive the knife pusher shaft distally through tissue after the knife pusher shaft has bent relative to the longitudinal axis of the elongate shaft.

18. The method of claim 15, further comprising activating the actuation mechanism to rotate a gear within the surgical device, the gear driving a rack housing and the knife pusher shaft coupled thereto to move a cutting element through the first and second jaws and thereby cut tissue engaged therebetween.

19. The method of claim 15, wherein actuating the closure mechanism comprises moving a movable handle toward a stationary handle.

20. The method of claim 19, wherein the jaw closure shaft moves proximally through the knife pusher shaft when the movable handle is moved toward the stationary handle.

\* \* \* \* \*